(12) United States Patent
Abrahamsson

(10) Patent No.: US 8,602,990 B2
(45) Date of Patent: Dec. 10, 2013

(54) METHOD AND DEVICE FOR MICRODIALYSIS SAMPLING

(75) Inventor: Pernilla Birgitta Abrahamsson, Umeå (SE)

(73) Assignee: MD Biomedical AB, Umea (SE)

( * ) Notice: Subject to any disclaimer, the term of this patent is extended or adjusted under 35 U.S.C. 154(b) by 1005 days.

(21) Appl. No.: 12/633,586

(22) Filed: Dec. 8, 2009

(65) Prior Publication Data

US 2010/0152555 A1    Jun. 17, 2010

Related U.S. Application Data

(60) Provisional application No. 61/120,849, filed on Dec. 9, 2009.

(51) Int. Cl.
*A61B 5/00* (2006.01)

(52) U.S. Cl.
USPC .......................................................... 600/309

(58) Field of Classification Search
USPC .......................................................... 600/309
See application file for complete search history.

(56) References Cited

U.S. PATENT DOCUMENTS

| | | | |
|---|---|---|---|
| 6,463,312 B1* | 10/2002 | Bergveld et al. | 600/345 |
| 2003/0014049 A1* | 1/2003 | Koblish et al. | 606/41 |
| 2004/0162467 A1* | 8/2004 | Cook | 600/309 |
| 2005/0273138 A1* | 12/2005 | To et al. | 606/219 |
| 2006/0079740 A1* | 4/2006 | Silver et al. | 600/309 |
| 2008/0269573 A1* | 10/2008 | Najafi et al. | 600/301 |
| 2009/0209950 A1* | 8/2009 | Starksen | 606/21 |
| 2011/0213230 A1* | 9/2011 | Lindgren et al. | 600/365 |

FOREIGN PATENT DOCUMENTS

WO    WO 2007/126380    *    8/2007

\* cited by examiner

*Primary Examiner* — Rodney Fuller

(57) ABSTRACT

Microdialysis sampling methods utilizing at least one microdialysis probe placed on the surface of a vital human or animal organ for sampling metabolic substances that indicate the metabolic conditions of the organ from the surface of the organ. The invention further relates to microdialysis sampling probes for sampling metabolic substances, said probes being adapted to be attached to the surface of a vital human or animal organ.

9 Claims, 13 Drawing Sheets

METHOD AND DEVICE FOR MICRODIALYSIS SAMPLING

TECHNICAL FIELD

The present invention concerns a method and device for microdialysis sampling the well-being or metabolic conditions of vital organs within humans and animals. More specifically the present invention regards the measurement of substance concentrations (molecules) on the surface of vital organs in accordance with the claims.

BACKGROUND OF THE INVENTION

Microdialysis is a means of sampling substances from the body to help clinicians assess well-being or metabolic conditions by providing serial biochemical samples from a catheter which lies within the substance of an organ. Current commercial microdialysis systems are equipped for sample collection, handling, and analysis of small molecules including glucose, lactate, pyruvate and glycerol as markers of cell injury. Sample collection is based on passive diffusion through a semi-permeable membrane placed at the end of a catheter.

Microdialysis sampling can be performed on organs which move. For example microdialysis sampling can be used to study metabolic aspects of the beating heart. When a microdialysis probe is placed into the substance of a beating heart, there is always concern that the catheter position can be disturbed by the heart's contractions as well as risk for damage to heart tissue as well as the catheter when inserting the microdialysis probe. These risks are taken because it has been shown that the microdialysis technique gives a more rapid response compared to ECG monitoring, catecholamine analyses or other clinical signs of cardiac ischemia.

When a microdialysis catheter is placed in a tissue or organ, there will unavoidably be some tissue damage. If the microdialysis method is used clinically to monitor for example a myocardial metabolic state, it is important to minimize the damage associated with probe insertion. The tissue damage caused by probe placement makes it necessary to allow an equilibration period of 60 to 90 minutes before reliable data can be obtained and this is done in order to allow local resorption or redistribution of fluid that may have initially accumulated surrounding the catheter at the time of insertion. If the time needed for this equilibration period could be shortened or eliminated altogether, this would allow for a more efficacious clinical application of microdialysis sampling.

There is a clear need for a device and method that can sample changes in interstitial fluid concentrations of small molecules which agree strongly with microdialysis sampling direct from the interstitium which alleviates the above mentioned problems associated with microdialysis sampling from a probe placed in the substance of an organ, for example the heart wall.

PRIOR ART

Langemann introduced the microdialysis technique for studies in association with human cardiac surgery in 1996. He placed the catheter in the left ventricular wall and showed that it was possible to measure serial changes in glucose and lactate in the myocardium.

The Swedish patent document SE434214 titled, "Dialysis Probe for Insertion in Living Tissue—has Membrane Surrounded by Stiffening Casing" describes a dialysis probe, primarily intended for insertion in biological tissues, for example brain tissue, which is comprised of a dialysis membrane and ducts for flow of the perfusion fluid over the membrane. The dialysis membrane in such a probe can be surrounded by a mounting which supports and partially reveals the membrane, and which is more rigid than the membrane. This design has a clear disadvantage compared with the present invention because it does not incorporate a method that allows for microdialysis sampling by the placement of the catheter and/or probe on the surface of the organ to be sampled. Furthermore the design is not intended for organs that contract, expand or in some way move.

The patent document EP0742725B1 applied for by MICRODIALYSIS HOLDING AB titled, "Microdialysis Probe having Reinforced Tube—Comprises a Dialysis Tube over Centre Tube having Enlarged Distal End to Remove Probe Intact" describes a microdialysis probe having a center tube surrounded by a thin dialysis tube, which is located between two tubular fitting parts. The purpose of which is to reinforce the probe and facilitate its withdrawal without any part of the probe remaining. Despite the fragility of the dialysis tube, the distal end of the center tube from within is fixedly joined to the distal fitting part, which also has a larger diameter than the dialysis tube. The design is essentially different from the present invention because it does not incorporate a method that allows for microdialysis sampling by the placement of the catheter and/or probe on the surface of the organ to be sampled.

The Swedish patent document SE511932 titled, "Catheter for Insertion into Blood Vessel to Detect Substances in Coronary Sinus Related to Metabolic Changes in Heart" describes a catheter that is to be inserted into a blood vessel and guided by said blood vessel. The catheter is comprised of an essentially cylindrical wall structure which defines an elongated catheter body having a proximal end and a distal end, an opening formed in said cylindrical wall structure which extends into said catheter body forming a microdialysis chamber therein having a proximal and distal end. The microdialysis membrane covering said opening such that said microdialysis chamber has at least a portion of said microdialysis membrane as part of its wall, first and second channels extending through at least a portion of said catheter body and having proximal and distal ends, a cross channel connecting one of said first or second channels to the more distal side of said microdialysis chamber and the other of said first or second channels connected to the more proximal side of said microdialysis chamber. The said proximal ends of said first and second channels are connected to an external means for circulating, monitoring and analyzing a microdialysis solution passing there through. The design differs greatly from the present invention because it is intended to be inserted into a body part does not incorporate a method that allows for microdialysis sampling by the placement of the catheter and/or probe on the surface of the body part to be sampled.

BRIEF DESCRIPTION OF THE INVENTION CONCEPT

The main objective of the present invention is to achieve a considerable improvement in the above mentioned drawbacks with current techniques. This is achieved by using a device in accordance with the patent claims' characteristic parts. Another aim of the present invention is to create a reliable, safe and efficient device and method for microdialysis sampling. A further objective of the present invention is to achieve a stable method for measuring metabolic changes postoperatively.

DESCRIPTION OF THE INVENTION

The invention will be described in detail in the following text with reference to the enclosed tables and drawings that in an exemplifying purpose show the current preferred embodiments of the invention.

FIG. 1 shows the glucose concentrations during a control period followed by an ischemic period (time 220-270 minutes). Microdialysis probes were placed in the myocardium (filled triangle) and on the surface of the epicardium (open square). Data are presented as mean±SEM. n=10.

FIG. 2 shows lactate concentrations during a control period followed by an ischemic period (sample 220-270 minutes). Microdialysis probes were placed in the myocardium (filled triangle) and on the surface of the epicardium (open square). Data are presented as mean±SEM, n=10.

FIG. 3 shows the pyruvate concentrations during a baseline period followed by an ischemic period (sample 220-270 minutes). Microdialysis probes were placed in the myocardium (filled triangle) and on the surface of the epicardium (open square). Data are presented as mean±SEM, n=10.

FIG. 4 shows glycerol concentrations during a baseline period followed by an ischemic period (sample 220-270 minutes). Microdialysis probes were placed in the myocardium (filled triangle) and on the surface of the epicardium (open square). Data are presented as mean±SEM, n=9.

FIG. 5 shows the glucose concentrations during a short ischemic period followed by a longer ischemic period (sample 220-270 minutes). Microdialysis probes were placed in the myocardium (filled triangle) and on the surface of the epicardium (open square). Data are presented as mean±SEM, n=9.

FIG. 6 shows the lactate concentrations during a short ischemic period followed by a longer ischemic period (sample 220-270 minutes). Microdialysis probes were placed in the myocardium (filled triangle) and on the surface of the epicardium (open square). Data are presented as mean±SEM, n=9.

FIG. 7 shows pyruvate concentrations during a short ischemic period followed by a longer ischemic period (sample 220-270 minutes). Microdialysis probes were placed in the myocardium (filled triangle) and on the surface of the epicardium (open square). Data are presented as mean±SEM, n=9.

FIG. 8 shows glycerol concentrations during a short ischemic period followed by a longer ischemic period (sample 220-270 minutes). Microdialysis probes were placed in the myocardium (filled triangle) and on the surface of the epicardium (open square). Data are presented as mean±SEM, n=9.

Figure 9:
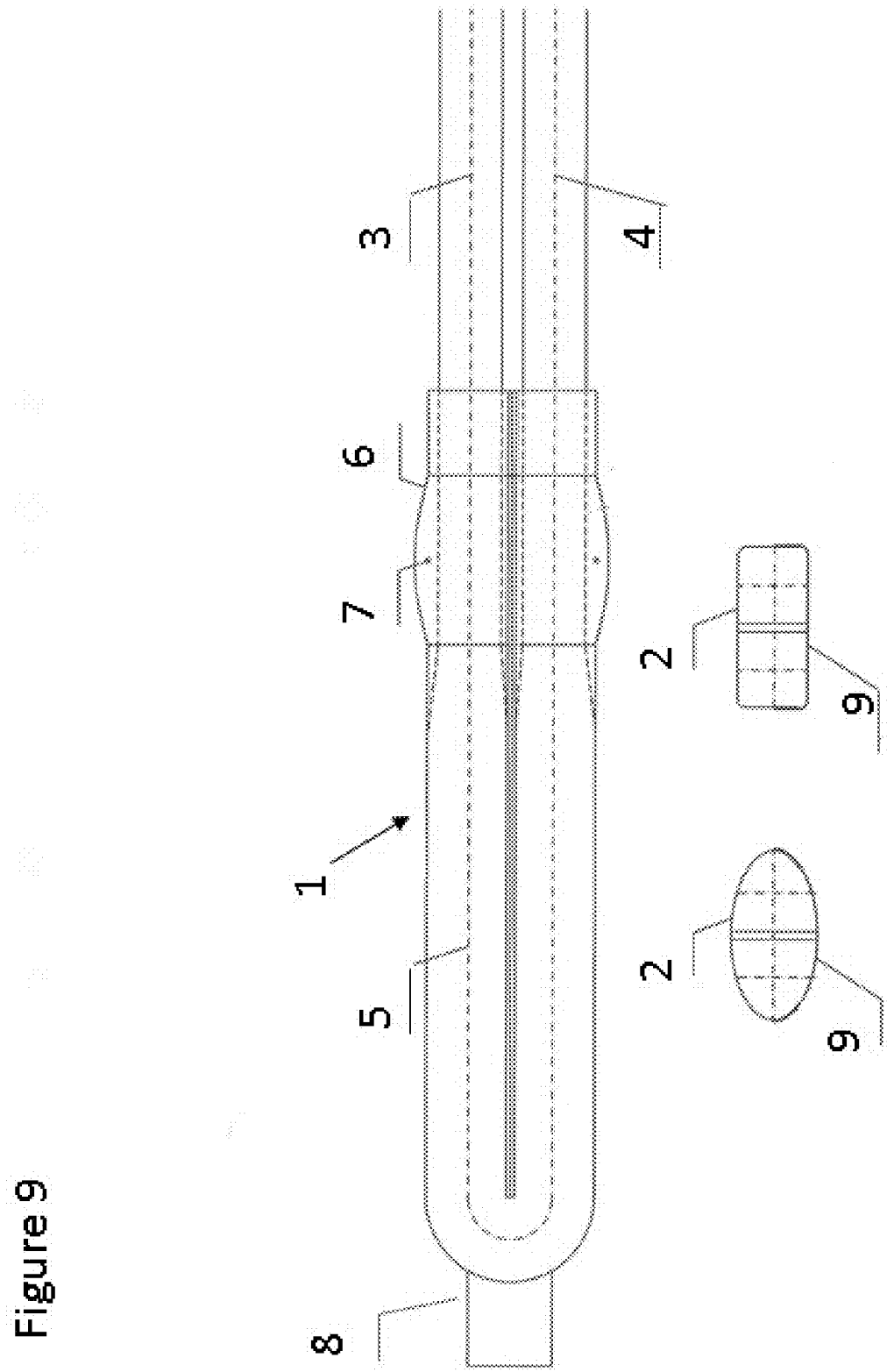
FIG. 9 shows a first preferred embodiment of the present invention.

By utilizing the method of the present invention a probe/catheter is placed on the surface of a vital organ and it samples substances that follow relatively rapid metabolic changes in the organ which previously required that a catheter be placed in the substance of the organ to collect the samples. According to the first preferred embodiment of the present invention as shown in FIG. 9, a probe/catheter 1, of an elliptical, rectangular or other for the purpose suitable shape, is comprised of an outer casing 2 with an inlet 3 and an outlet 4 that are intended to be connected to a pump by tubing. The pump and tubing suitable for the purpose are of current designs and are therefore not shown in the figures or discussed further in detail.

The pump and tubing are intended for providing a flow of suitable fluid such as perfusion fluid (perfusate) or similar through the probe 1. Within the probe 1 is a U-shaped channel 5 that connects the inlet 3 with the outlet 4. The channel 5 is designed to allow perfusion fluid (perfusate) or similar to flow through the probe 1. The channel 5 may consist of a tube or other suitable for the purpose hollow design. According to the first preferred embodiment of the present invention as shown in FIG. 9 an attachment girdle 6 designed to facilitate the attachment of the probe 1 to the tissue surface of an organ using at least one suture via at least one lateral hole or eyelet 7 is integrated onto the outer casing 2 of the probe 1. On the end of the probe 1 opposite the inlet 3 and outlet 4 is placed a ring 8 also designed for securing the probe 1 to an organ via at least one suture. A semi-permeable membrane 9 is attached to the underside of the probe 1, the side facing the organ.

Figure 10:
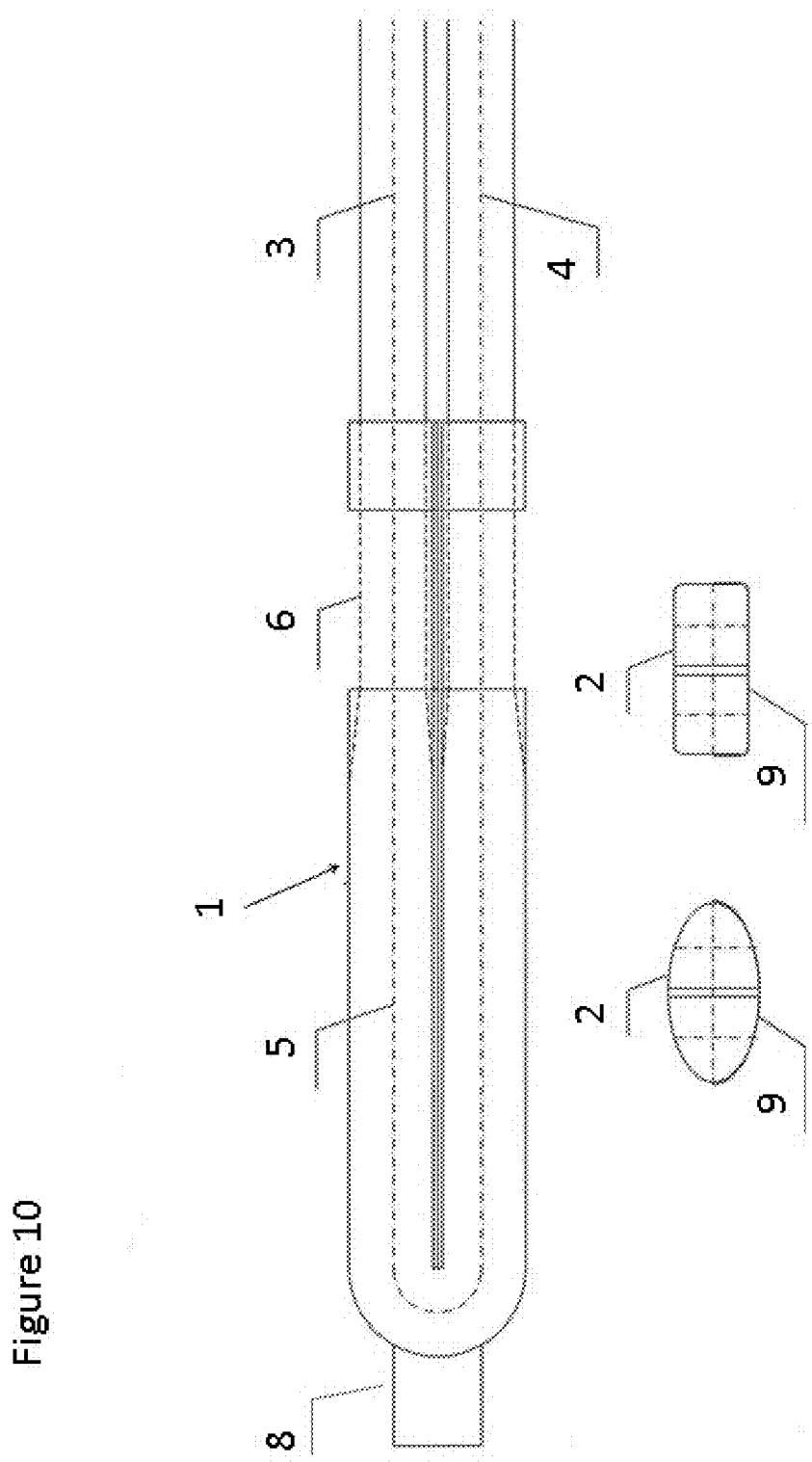
FIG. 10 shows a second preferred embodiment of the present invention.

According to the second preferred embodiment of the present invention as shown in FIG. 10, a probe/catheter 1, of an elliptical, rectangular or other for the purpose suitable shape, is comprised of an outer casing 2 with an inlet 3 and an outlet 4 that are intended to be connected to a pump by tubing. Within the probe 1 is a U-shaped channel 5 that connects the inlet 3 with the outlet 4. In all the preferred embodiments except the embodiment shown in FIG. 9 the attachment girdle 6 is essentially in the form of a recess in the outer casing 2 and does not contain eyelets 7. Attachment of the probe 1 to the tissue surface of an organ is accomplished by using at least one suture placed in the recess of the attachment girdle 6. In this way the suture may contain several millimeters of slack, preferably within an interval of three to eight millimeters, so that the probe/catheter 1 is not subjected to large mechanical forces relating to a beating or moving organ such as the heart. On the end of the probe 1 opposite the inlet 3 and outlet 4 is placed a ring 8 also designed for securing the probe to an organ via at least one suture. A semi-permeable membrane 9 is attached to the underside of the probe 1, the side facing the organ. It is conceivable that several other embodiments of the catheter/probe 1 which are suitable for the method can be used.

Figure 11:
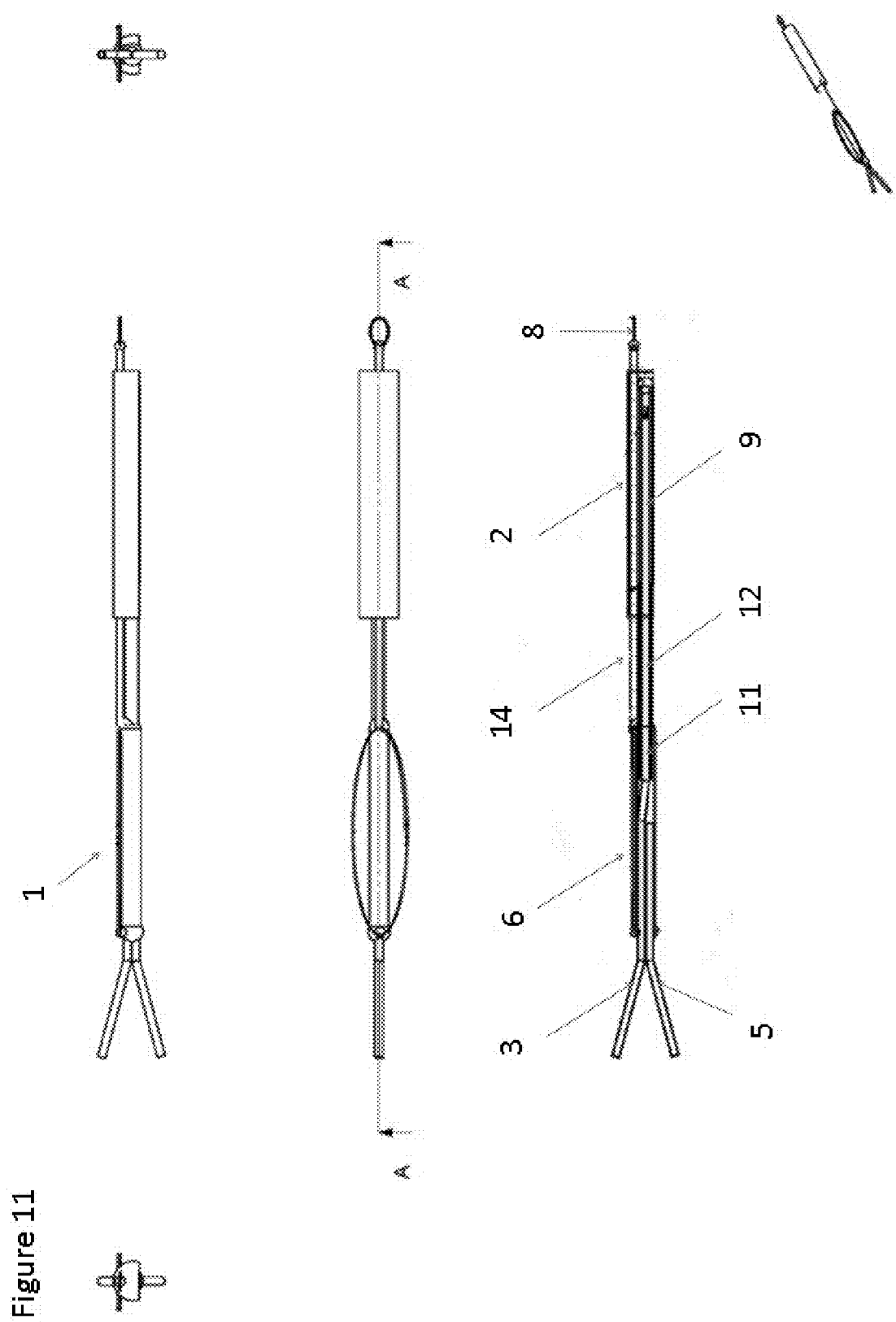
FIG. 11 shows a third preferred embodiment of the present invention.

A third preferred embodiment of the present invention is shown in FIG. 11. FIG. 11 shows a probe/catheter 1 with a tube in the inlet 3 that is intended to be connected to a pump (not shown). Via a preferably concentric tube the perfusion fluid flows into the inlet 3 to the probes 1 distal end allowing the fluid to come into contact with the semi-permeable membrane 9. At the crossover point 11 the fluid then passes through to the outlet 4 into tubing leading to a vial were the liquid is intended to be collected. The tubes leading to and from the inlet 3 and outlet 4 are inserted in the first shaft 12 and secured by suitable means for example gluing to the liquid crossover point 11 and an attachment girdle 6. A second shaft 14 is fixed upon the membrane 9 and also attached to the liquid crossover point 11 and the attachment girdle 6. On the end of the second shaft 14 a ring 8 is placed for temporarily securing the probe 1 to an organ via at least one suture. An attachment girdle 6 is designed to facilitate the temporary attachment of the probe 1 to the tissue surface of an organ using at least one suture around the attachment girdle 6. The suture or sutures may be placed so it/they will be able to move along the attachment girdle 6 to avoid damage to the probe and/or tissue. To reduce evaporation and possible interface with other organs an outer casing 2 covers the probe 1.

Figure 12:
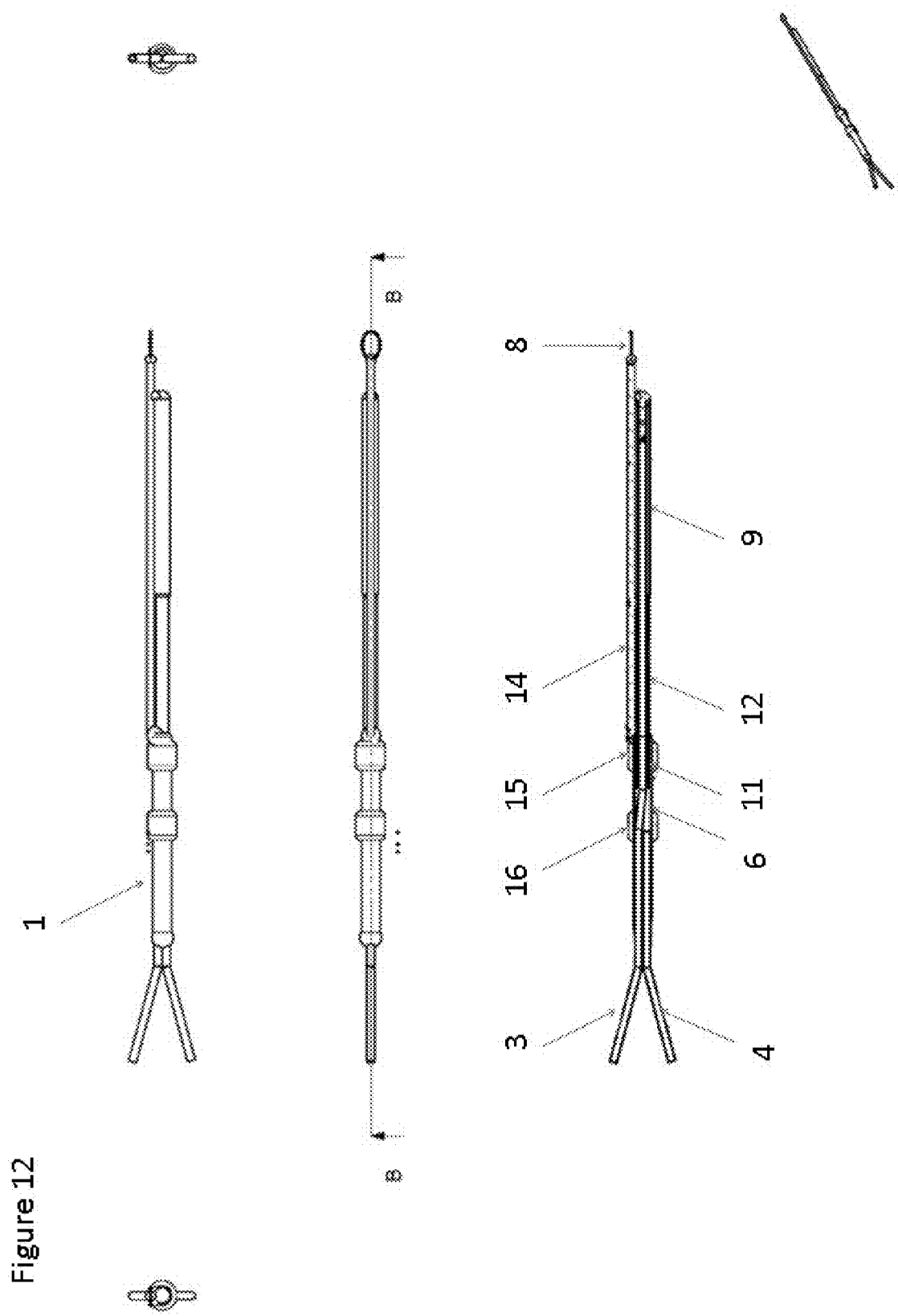
FIG. 12 shows a fourth preferred embodiment of the present invention.

A fourth preferred embodiment of the present invention is shown in FIG. 12. FIG. 12 shows a probe/catheter 1 with a tube in the inlet 3 that is intended to be connected to a pump (not shown). Via a preferably concentric tube the perfusion fluid flows into the inlet 3 to the probes 1 distal end allowing the fluid to come into contact with the semi-permeable membrane 9. At the crossover point 11 the fluid then passes through to the outlet 4 into tubing leading to a vial were the liquid is intended to be collected. The tubes in the inlet 3 and outlet 4 are inserted in the first shaft 12 and secured by suitable means to the liquid crossover point 11 for example by being glued to the attachment elements 15 and 16. The second shaft 14 is fixed upon the membrane 9 and into the liquid crossover point 11 and attachment elements 15 and 16. On the end of the second shaft 14 a ring 8 is placed for temporarily securing the probe to an organ via at least one suture. An attachment girdle 6 between attachment element 15 and 16 is designed to facilitate the temporary attachment of the probe to the tissue surface of an organ using at least one suture around the attachment girdle 6. The suture or sutures may be placed so it/they will be able to move between the attachment elements 15 and 16 to avoid damage of the probe and/or organ tissue.

Figure 13:
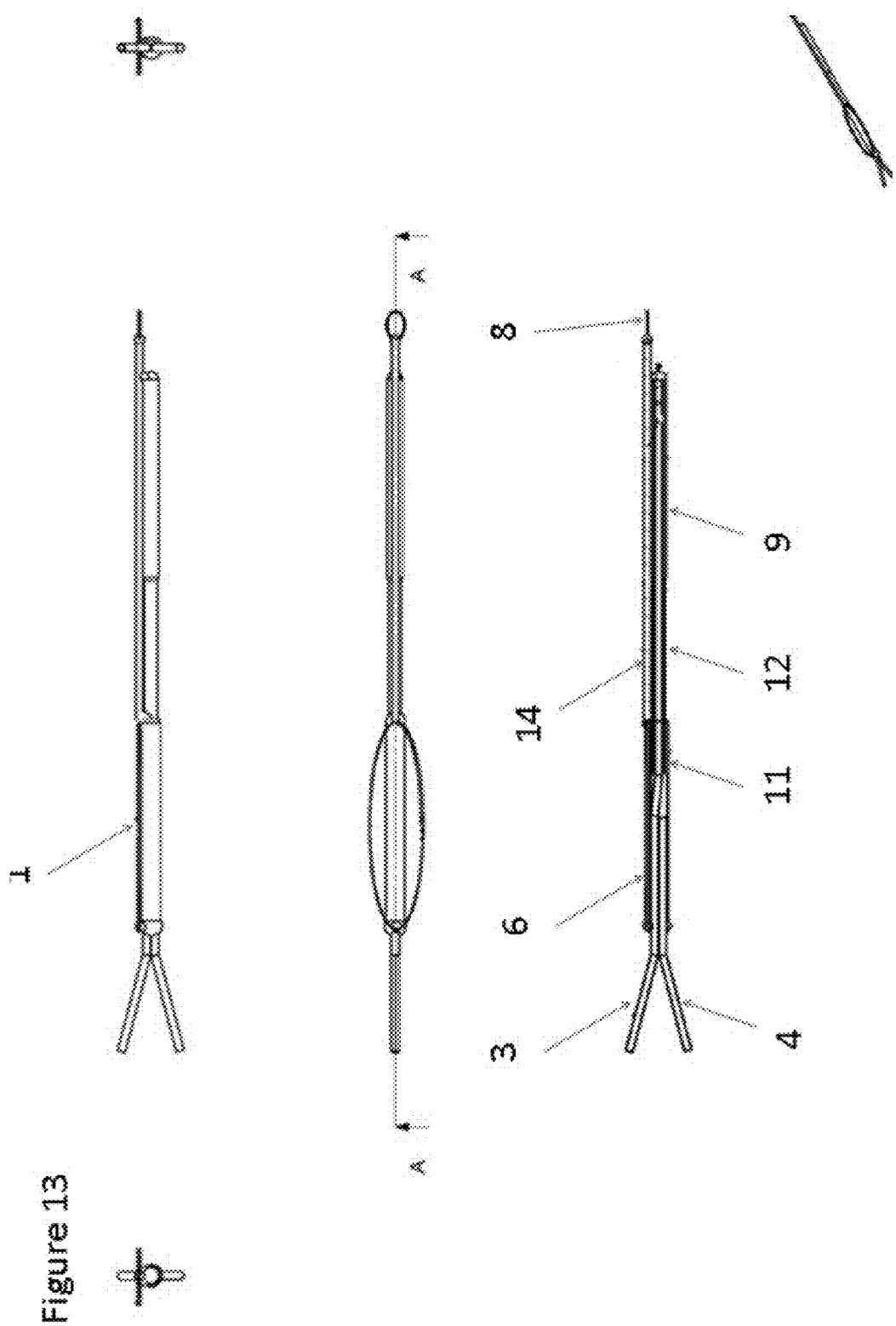
FIG. 13 shows a fifth preferred embodiment of the present invention.

A fifth preferred embodiment of the present invention is shown in FIG. 13. FIG. 13 shows a probe/catheter 1 with a tube in the inlet 3 that is intended to be connected to a pump (not shown). Via a preferably concentric tube the perfusion fluid flows into the inlet 3 to the probes 1 distal end allowing the fluid to come into contact with the semi-permeable membrane 9. At the crossover point 11 the fluid then passes through to the outlet 4 into tubing leading to a vial were the liquid is intended to be collected. The tubes leading to and from the inlet 3 and outlet 4 are inserted in the first shaft 12 and secured by suitable means to the liquid crossover point 11 and an attachment girdle 6 for example by being glued to the second shaft 14. On the end of the second shaft 14 a ring 8 is placed for temporarily securing the probe 1 to an organ via at least one suture. An attachment girdle 6 is designed to facilitate the temporary attachment of the probe 1 to the tissue surface of an organ using at least one suture around the attachment girdle 6. The suture or sutures may be placed so it/they will be able to move along the attachment girdle 6 to avoid damage to the probe 1 and/or organ tissue.

The idea for this unconventional site of microdialysis sampling came about after a serendipitous collection of microdialysis samples from a probe which relocated itself from an intestinal placement to an epicardial position accidentally, and, unexpectedly, analysis of samples from the epicardial catheter were similar to the other catheters which were attached by current techniques in the substance of the organ.

Testing shows that it is possible to place the microdialysis probe 1 of the present invention on the epicardial surface and recover samples reflecting the myocardial metabolic state of the organ. Testing has also shown that it is possible to measure rapid changes in concentrations especially for lactate where an ischemia period as short as ten minutes resulted in detectable increases in lactate concentrations. There was a similar pattern in lactate concentrations between samples analyzed from the myocardial and epicardial probes. A similar pattern was found when analyzing glucose and glycerol concentrations in paired samples.

The microdialysis catheter 1 of the present invention is configured with a catheter which lies relatively flat against the organ's surface, in order to have a larger contact area between the catheter 1 and the organ. In the preferred embodiments shown in FIGS. 9 and 10 the membrane 9 lies essentially on the underside (the side facing the organ) of the catheter 1, in order to avoid evaporation of microdialysate which can lead to artifactual concentration increases. This preferred design also provides more reliability in sampling because a steady state between the catheter 1 and the organ surface is reached more quickly. In the preferred embodiments shown in FIGS. 11, 12 and 13, the membrane's 9 side, the side facing away from the organ being sampled is covered so as not to come into contact with surrounding organs. The establishment of a steady state for sampling, during for example a heart operation, is necessary if the technique is to be used during the rest of the operation.

In the preferred embodiments in FIGS. 10, 11 and 12 the catheter's membrane 9 is glued to the outer casing 2 which will be constructed of a less elastic/flexible material so that the catheter 1 will resist folding or bending during placement and sampling periods. The probe/catheter 1 is temporarily attached to an organ surface, by at least one suture to the attachment girdle 6 in a manner that allows for several millimeters of slack so that the catheter 1 is not subjected to large mechanical forces relating to a beating or moving organ. At the catheter's tip/end, a small ring 8 is used to temporarily attach the catheter's tip/end to an organ surface with at least one suture, so that the catheter's membrane 9 is held stationary on the organ surface. The catheter 1 is designed with no structures which can catch or fasten themselves to tissue so that it can be easily removed through an operative incision in the post operative period without causing any tissue injury. The catheter 1 is coupled to a pump which generates a constant flow of fluid or perfusate over the membrane 9 area. The fluid is pumped in through the tubes into the inlet 3, flows through the entire catheter 1, and then flows out through the tubes from the outlet 4.

The membrane 9 of the present invention consists preferably of a polymer composition such as for example PAES (polyarylethersulfone). The tubes from and to the inlet 3 and outlet 4 consist preferably of a polymer material, for example PUR (polyurethane). The outer casing 2 consists preferably of a polymer material as for example polyurethane, polyamide or polyimide. Other materials than the ones mentioned, that are suitable for the purpose, may of course also be used for the probe and its parts.

Test Case

The case study was approved by the Animal Experimental Ethics Committee at Umeå University Sweden, and was conducted in accordance with the (Guide for the Care and Use of Laboratory Animals, National Research Council, Washington, USA, 1996) NIH Institutional animal care and use committee guidebook. A total of 19 female pigs were used.

After intramuscular premedicination, with a mixture of ketamine 10 mg/kg (Ketalar®, Pfizer, Morris Plains, N.J., USA), Rompum (Xylazine) and atropine sulphate 0.05 mg/kg (Atropin, NM, Pharma, Stockholm, Sweden) anaesthesia was introduced by an intravenous bolus dose of 10 mg/kg sodium pentobarbital (Pentobarbitalnatrium, Apoteksbolaget, Stockholm, Sweden). Infusion of Fentanyl 20 µg/kg/h (Fentanyl, Braun, Melsungen, Germany), Midazolam 0.3 mg/kg/h (Dormicum, Roche, Basel, Switzerland) and sodium pentobarbital 5 mg/kg/h was used for maintainenance of anaesthesia. The animals were tracheotomized (7.0 OP endotracheal tube, Rusch, kernen, Germany) and mechanically ventilated with air containing 30% oxygen (Evita 4, Dräger, Germany) and adjusted to normoventilation as measured with intermittent arterial blood gas analyses (ABL 5 autoanalyzer, Radiometer, Copenhagen, Denmark). One liter of Ringer's acetate (Pharmacia-Upjohn, Sweden) was given to the animals during the first hour followed by an infusion that started at 15 ml/kg/h. The infusion was increased during the day to maintain normovolemia, as determined by the goal to achieve a CVP between 5 and 10 mmHg.

In brief, an arterial catheter was placed in a small neck artery and a central venous catheter was inserted in the external jugular vein. Basal registration included measurement of heart rate (HR), mean arterial pressure (MAP) and central venous pressure (CVP). All pressures were measured using fluid filled catheters and pressure transducers (Ohmeda Inc., USA) at the mid-axillary's level. Data was continuously recorded using a computer based multi-channel signal acquisition and analysis system (Acknowledge, Biopac system Inc., CA, USA).

A medial sternotomy was then performed and a diagonal branch of the left anterior descending (LAD) artery was identified. A Gore-tex suture snare was placed around the proximal aspect of the branch. One microdialysis probe (CMA 20 PEAS Elite, CMA Microdialysis, Solna, Sweden) was placed in the myocardial tissue supplied by the snared LAD branch using a modified Seldinger technique was used in order to minimise mechanical injury to the microdialysis probe and to the myocardium. Another microdialysis probe (CMA 20 PEAS Elite, CMA Microdialysis, Solna, Sweden) was placed on the epicardial surface above the first myocardial probe. The epicardial probe was secured with sutures at the suture point and over the membrane.

The microdialysis probes were perfused with Ringers solution (a modified Krebs-Ringer phosphate buffer) at a flow rate of 2.0 μl/min. Samples were collected every 10th minute during the equilibration period and throughout the study protocol. Animals were randomized in two groups for a protocol involving another study (for which microdialysis was employed here as a sampling method). One group had a 150 minutes period without any intervention before 40 minutes of ischemia induced by tightening the Gore-tex suture. The second group had four 10 minute periods of snare occlusion followed by 20 minutes of reperfusion before the 40 minutes ischemic period.

52 samples were collected for each animal, 26 from each probe. Glucose, lactate, pyruvate and glycerol were analysed in a CMA 600 analyser (CMA, Solna, Sweden). The analyser is a clinical chemical analyser that uses enzymatic reagents and colorimetric measurements of the microdialysis samples. All samples were collected in glass vials and sealed with a crimp cap directly after sampling. The samples were stored in 4-6° C. no longer than one day. All samples were centrifuged (Mini Galaxy, VWR, West Chester, Pa., USA) for 30 seconds before analyses.

Microdialysis analysis was performed on sample from the area affected by the coronary artery occlusion for detection of metabolic by products related to myocardial ischemia and reperfusion. All results were paired, one from the microdialysis probe in the substance of the heart wall, and the other result from the probe lying on the surface of the ventricular wall adjacent to the first probe.

Figure 1:
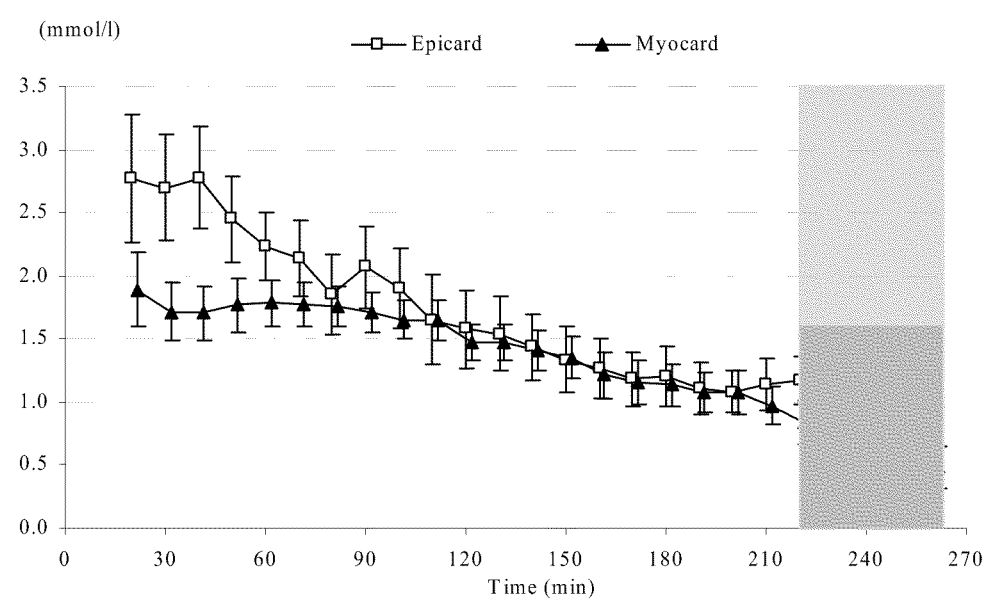

Glucose concentrations measured from the epicardial surface showed more variation during the equilibration period (time 20-50 minutes) than concentrations measured in the myocardium. After the equilibration period (60 minutes), glucose levels were similar in both probes and showed also a similar pattern, with decreasing glucose concentration during the resting period, and then also during ischemia (FIG. 1).

Figure 2:
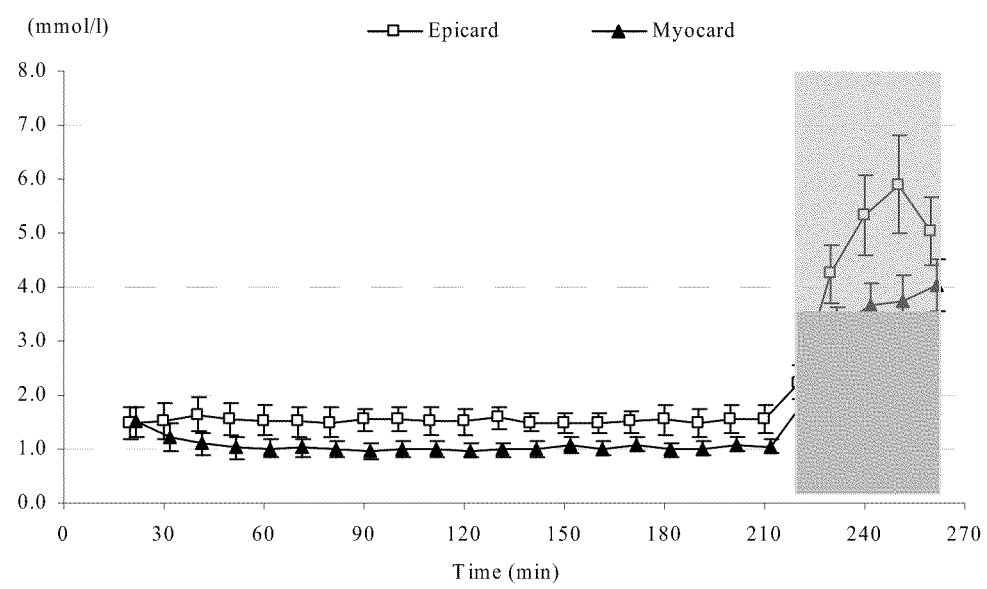

Also lactate concentrations followed the same pattern in both probes. However, concentrations were higher in the epicardial probe than in the myocardial probe during the 40 minutes final ischemia period (FIG. 2).

Figure 3:
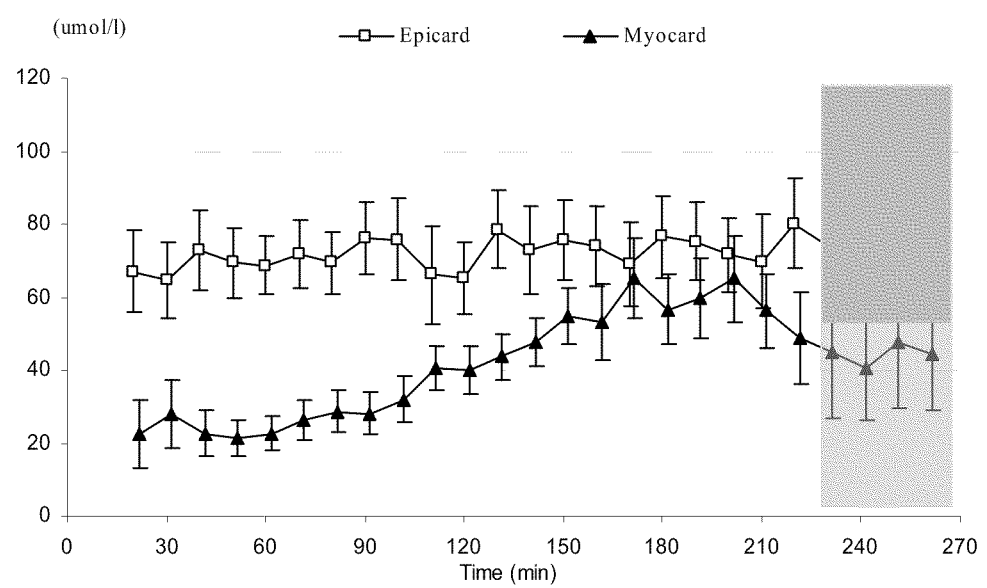

There was a discrepancy in pyruvate concentrations as measured by the two different probes. Thus, pyruvate concentrations measured by the epicardial probe were similar throughout the study period, while pyruvate concentrations measured in the myocardium showed a dual pattern, with a gradual increase until a final decrease during the index ischemia period (FIG. 3).

Figure 4:
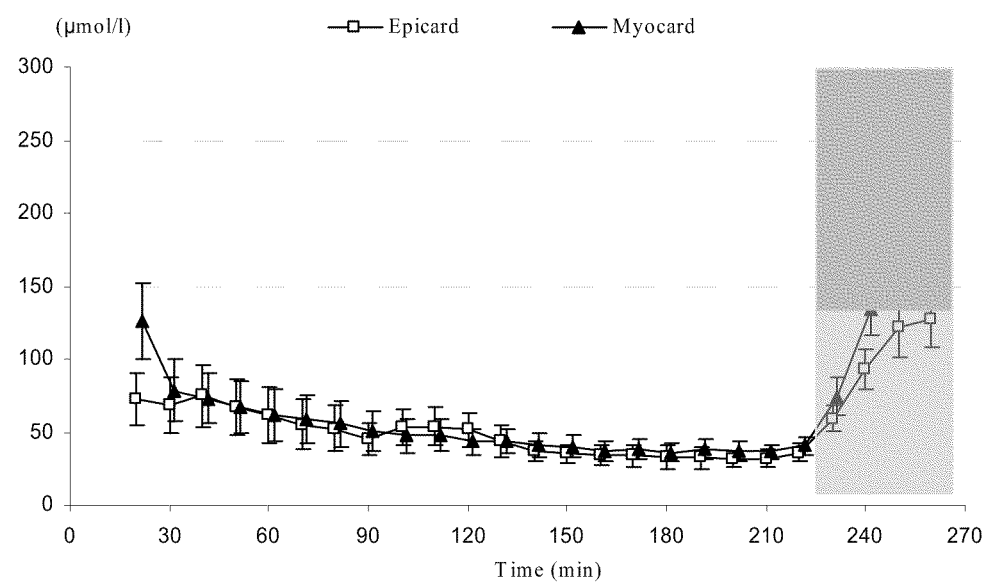

Glycerol concentrations were stable during the equilibration and baseline periods with an increase during the 40 minutes ischemia period. The epicardial and myocardial probes followed a similar pattern (FIG. 4).

Figure 5:
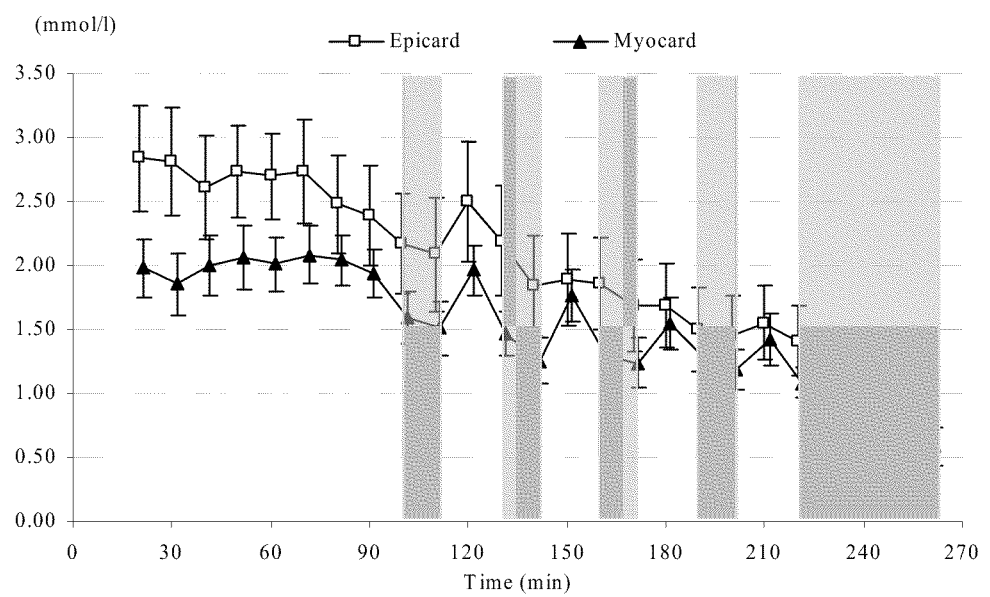

Glucose concentrations measured from the epicardial surface during equilibration and baseline periods were less stable in this group of animals with several ischemic periods compared with the concentrations in the myocardial probe. Glucose decreased similarly in both probes during the study protocol (FIG. 5). Rapid changes in glucose concentrations were difficult to detect in samples from the epicardial probe compared to the myocardial probe.

Figure 6:
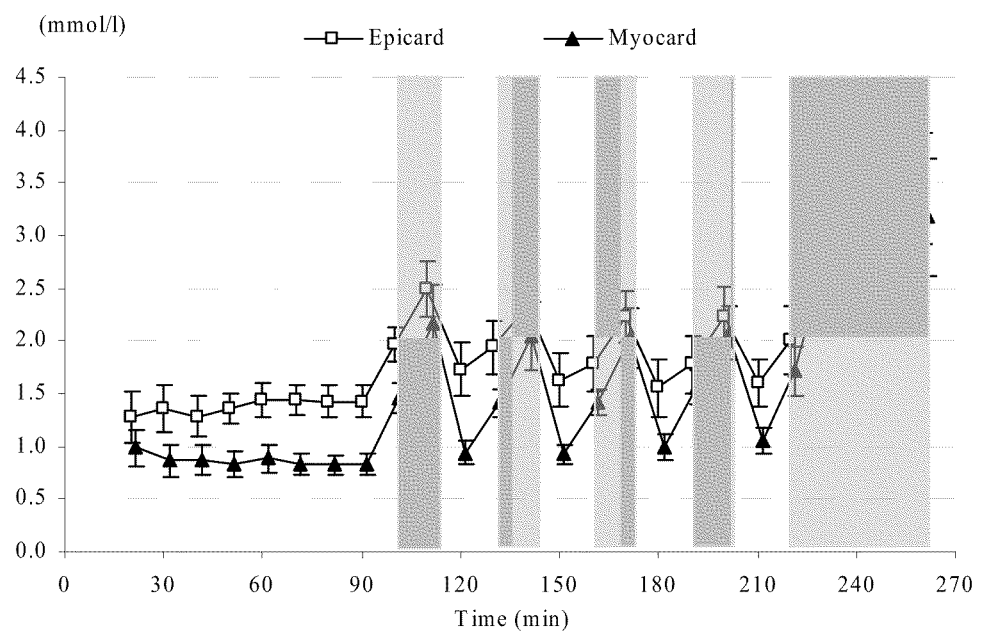

Lactate concentrations were stable during the initial equilibration period as measured by both probes. In both probes, lactate concentrations increased in association with ischemia period and decreased during reperfusion (FIG. 6).

Figure 7:
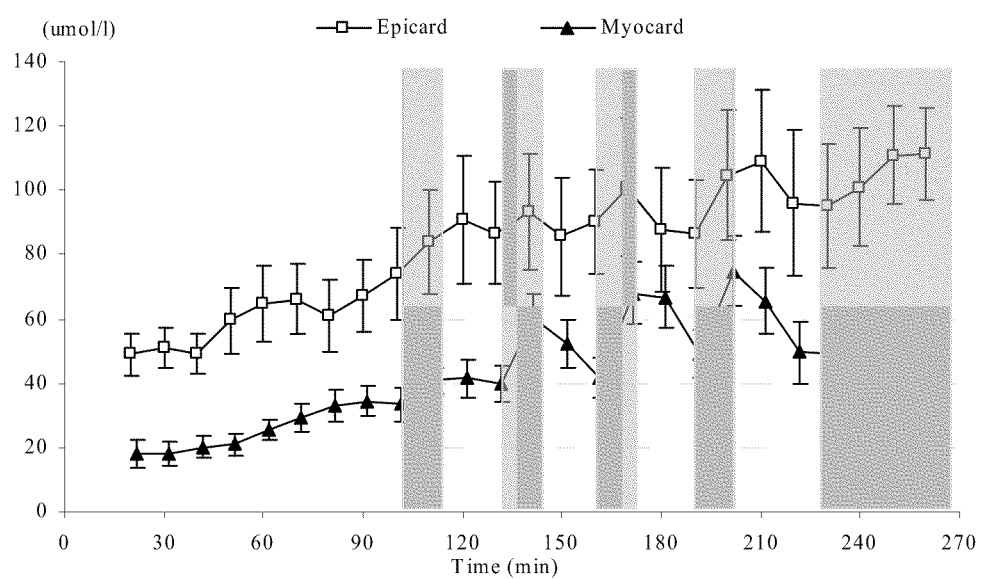
Figure 8:
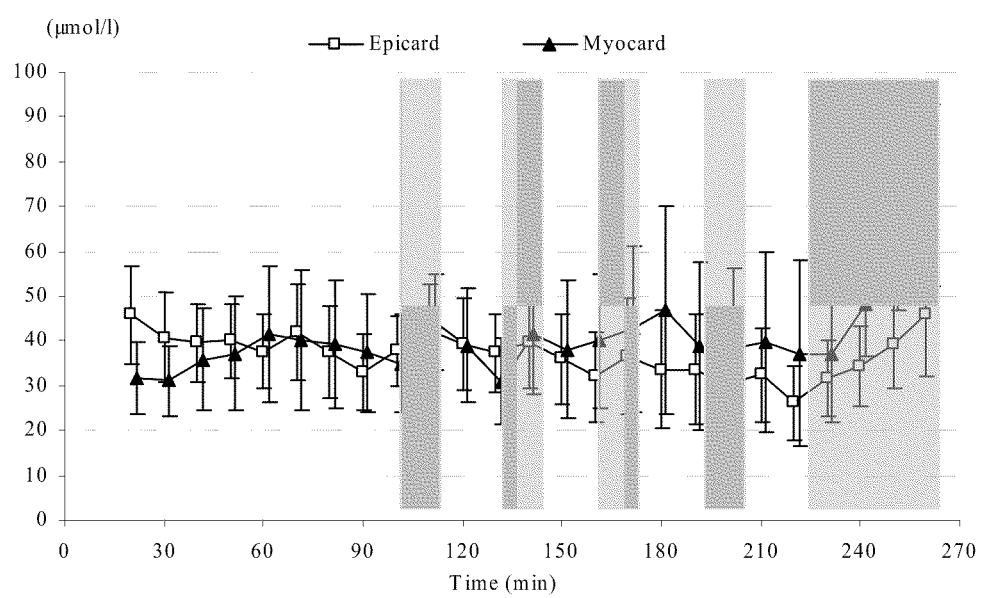

Pyruvate concentrations continuously increased during the experimental protocol as measured by both probes. The short ischemia periods were associated with increased pyruvate concentrations detected with the myocardial probe but not with the epicardial probe (FIG. 7). Concentrations of glycerol were rather unchanged in both probes during the protocol (FIG. 8). A small increase was observed during the final longer ischemia period.

Even if the preferred embodiment has been described in detail, variations and modifications within the scope of the invention can become apparent for professionals in the field and all these variations are considered to fall under the subsequent claims. Alternatively, different materials with suitable qualities can be applied to the entire, or a partial part of, the present invention. Alternatively, the shapes, dimensions and sizes of the described preferred embodiments may vary substantially. For example the size and shape of the attachment girdle 6, the attachment elements 15 and 16 and the ring 8 of the probe 1 may vary substantially and still be suitable for the purpose. Several alternative embodiments, for example of the catheter/probe's 1 shape or number of points of attachment to the organ as well as placement of the membrane 9 and so on are conceivable.

In alternative embodiments the membrane 9 may for example be designed in the form of a cylinder, and constructed using previously established methods. The aspect which distinguishes the present invention from previous designs is the zone in the catheter where the membrane 9 is placed on the catheter 1 (see above). In order to minimize evaporative microdialysate loss, and in order to more rapidly achieve a steady state of physiological substance concentrations across the catheter's membrane 9, it is conceivable that a protective (cover) which lies approximately 0.5 mm above the membrane 9 will sit and protect the membrane.

Advantages of the Invention

The present invention eliminates or greatly reduces problems with existing designs that were previously described in this patent application. The main advantage of locating the microdialysis probe on the epicardial surface is the minimal damage to the tissue or organ. This application lowers the risk for complications compared to when catheters are placed and removed from for example the myocardium. Although some clinical studies have shown that microdialysis catheters can be placed and removed from the myocardium without complications, the placement of a microdialysis catheter on the epicardium is safer especially for patients with myocardial injuries. Further, the epicardial approach of the present invention enables the catheter to be placed on for example the atria. The intramyocardial approach does not allow for sampling in the thin walled atriums. Another advantage aspect of probe location in the experimental settings is that it is easier to obtain an adequate and certain location on the epicardial surface than in the myocardium. Thus, the epicardial approach of the present invention reduces the risk of inadequate probe placement in conjunction with experimentally induced myocardial ischemia.

An additional advantage of the present invention is that there is virtually no need for equilibration time. Previous studies have shown equilibration times for known clinically-used microdialysis monitoring systems that vary from 60 to 90 minutes. Equilibration time depends on which substances that were analyzed and from which tissue the samples were collected. Clinical studies have shown that the equilibration time for glutamate was 30 minutes longer in injured patients than in healthy patients. With this in mind it is very advantageous to reduce or eliminate equilibration times both in healthy and injured patients.

Another advantage of the present invention is the virtual elimination of organ damage or bleeding related to the placement of microdialysis probes within solid organs using needles. Local bleeding at the insertion site adds to the equilibration time. Yet another advantage with microdialysis measurement on the heart surface which is made possible by the present invention is the possibility to continuously follow the metabolic state postoperatively. It has been shown that the microdialysis technique of the present invention provides a more rapid response compared to ECG monitoring, catecholamine analyses or other clinical signs of cardiac ischemia. This will lead to faster diagnostics and greatly minimize complications for patients during and after cardiac surgery. Furthermore the present invention allows for use of a very advantageous microdialysis technique for perioperative monitoring during cardiac surgery.

The invention claimed is:

1. Microdialysis sampling method utilizing at least one microdialysis probe (1) placed on the surface of a vital human or animal organ for sampling metabolic substances that indicate the metabolic conditions of the organ from the surface of the organ characterized by that the probe (1) is temporarily attached to the outside surface of the vital organ by at least one suture and not inserted into the substance of the vital organ, samples said metabolic substances via a semi-permeable membrane (9) attached to the probe (1), the side facing the surface of the organ.

2. Microdialysis sampling method according to claim 1 utilizing at least one microdialysis probe (1) placed on the surface of a vital human or animal organ for sampling metabolic substances that indicate the metabolic conditions of the organ from the surface of the organ characterized by that the probe (1) is temporarily attached to the vital organ by at least one suture with several millimeters of slack, preferably within an interval of 3 to 8 millimeters, in a recess in the attachment girdle 6 on the probe (1) so that the probe (1) is not subjected to large mechanical forces relating to a beating or moving organ.

3. Microdialysis sampling probe (1) for sampling metabolic substances via a semi-permeable membrane (9) attached to the probe (1), comprised of an outer casing (2) with an inlet (3) and an outlet (4) connected by a channel (5) that allows perfusion fluid to flow through the probe (1), characterized by that on the end or tip of the probe (1) opposite the inlet (3) and outlet (4) is placed a ring (8) designed for temporarily securing the probe to a vital organ via at least one suture.

4. Microdialysis sampling probe (1) according to claim 3 characterized by that an attachment girdle (6), designed to facilitate the temporary attachment of the probe (1) to the surface tissue of an organ via at least one eyelet (7) using at least one suture, is integrated onto the outer casing (2) of the probe (1).

5. Microdialysis sampling probe (1) according to claim 3 essentially of an elliptical, or rectangular shape.

6. Microdialysis sampling probe (1) according to claim 3 characterized by that the permeable membrane (9) is attached to the side of the probe (1) intended to be facing away from the organ is covered so as to reduce evaporation and possible interface or contact with other organs.

7. Microdialysis sampling probe (1) for sampling metabolic substances via a semi-permeable membrane (9) attached to the probe (1), comprised of an outer casing (2) with an inlet (3) and an outlet (4) connected by a channel (5) that allows perfusion fluid to flow through the probe (1), characterized by that the side of the permeable membrane (9) intended to be facing away from the organ is covered so as to reduce evaporation and possible interface or contact with other organs and further characterized by that on the end or tip of the probe (1) opposite the inlet (3) and outlet (4) is placed a ring (8) designed for temporarily securing the probe to an organ via at least one suture.

8. Microdialysis sampling probe (1) according to claim 7 characterized by that an attachment girdle (6), designed to facilitate the temporary attachment of the probe (1) to the surface tissue of an organ via at least one eyelet (7) using at least one suture, is integrated onto the outer casing (2) of the probe (1).

9. Microdialysis sampling probe (1) according to claim 7 essentially of an elliptical, or rectangular shape.

* * * * *